(12) United States Patent
Baker et al.

(10) Patent No.: US 11,179,554 B2
(45) Date of Patent: Nov. 23, 2021

(54) MICRONEEDLE ARRAY ASSEMBLY, DRUG DELIVERY DEVICE AND METHOD FOR ADMINISTERING LIQUID ACROSS A BROAD AREA AT LOW PRESSURE

(71) Applicant: SORRENTO THERAPEUTICS, INC., San Diego, CA (US)

(72) Inventors: Andrew T. Baker, Norcross, GA (US); Russell F. Ross, Jacksonville Beach, FL (US); Elizabeth Deibler Gadsby, Marietta, GA (US); Luke Hagan, Seattle, WA (US)

(73) Assignee: SORRENTO THERAPEUTICS, INC., San Diego, CA (US)

( * ) Notice: Subject to any disclaimer, the term of this patent is extended or adjusted under 35 U.S.C. 154(b) by 215 days.

(21) Appl. No.: 16/095,210

(22) PCT Filed: Apr. 17, 2017

(86) PCT No.: PCT/US2017/027879
§ 371 (c)(1),
(2) Date: Oct. 19, 2018

(87) PCT Pub. No.: WO2017/189258
PCT Pub. Date: Nov. 2, 2017

(65) Prior Publication Data
US 2019/0143090 A1   May 16, 2019

Related U.S. Application Data

(60) Provisional application No. 62/329,464, filed on Apr. 29, 2016.

(51) Int. Cl.
*A61M 37/00* (2006.01)

(52) U.S. Cl.
CPC . *A61M 37/0015* (2013.01); *A61M 2037/0023* (2013.01); *A61M 2037/0038* (2013.01); *A61M 2037/0061* (2013.01)

(58) Field of Classification Search
CPC ...... A61M 37/0015; A61M 2037/0023; A61M 2037/0038; A61M 2037/0061; A61K 9/0021
See application file for complete search history.

(56) References Cited

U.S. PATENT DOCUMENTS

2006/0184139 A1  8/2006  Quigley et al.
2007/0043320 A1  2/2007  Kenany
(Continued)

FOREIGN PATENT DOCUMENTS

JP   2013524985 A   6/2013
WO   2015168210 A1  11/2015

OTHER PUBLICATIONS

International Search Report and Written Opinion of International Application No. PCT/US2017/027879, dated Oct. 30, 2017, 16 pages.

(Continued)

*Primary Examiner* — Amber R Stiles
(74) *Attorney, Agent, or Firm* — Armstrong Teasdale LLP

(57) ABSTRACT

A uniformity control membrane can be securely engaged against an upstream side of a microneedle array and configured so that resistance to flow through the uniformity control membrane is substantially greater than the resistance to flow through the microneedle array. These differences in flow resistance can facilitate uniform administration of a liquid formulation into the patient's skin across a broad area and at a relatively low pressure, such as by way of capillary action. The administration of the liquid formulation into the patient's skin across the broad area can result from the liquid (Continued)

formulation being administered by way of at least a majority of the microneedles of the microneedle array.

11 Claims, 6 Drawing Sheets

(56) References Cited

U.S. PATENT DOCUMENTS

| | | |
|---|---|---|
| 2008/0257071 A1 | 10/2008 | Wimberger-Friedel et al. |
| 2013/0144257 A1 | 6/2013 | Ross |
| 2013/0165861 A1* | 6/2013 | Ross .................... A61B 17/205 |
| | | 604/173 |

OTHER PUBLICATIONS

Translation of JP Notice of Grounds for Rejection for JP Patent Application 2018-556459 drafted Feb. 19, 2021; 5 pp.
Extended European Search Report for EP Patent Application 21155203.9 dated Jun. 21, 2021; 7 pp.
Examination Report No. 2 for Patent Application AU 2017258749 dated Jul. 22, 2021; 4 pp.

\* cited by examiner

MICRONEEDLE ARRAY ASSEMBLY, DRUG DELIVERY DEVICE AND METHOD FOR ADMINISTERING LIQUID ACROSS A BROAD AREA AT LOW PRESSURE

CROSS-REFERENCE TO RELATED APPLICATIONS

This application is the national stage entry of PCT/US2017/027879, filed on Apr. 17, 2017, which claims the benefit of priority to United States Provisional Patent Application No. 62/329,464, filed Apr. 29, 2016, which are incorporated by reference in their entirety herein.

FIELD OF THE DISCLOSURE

The present invention generally relates to devices for delivering liquid formulations into a patient's skin. Particularly, this disclosure relates to devices having microneedle arrays for transdermal delivery of liquid formulations.

BACKGROUND

Numerous apparatuses have previously been developed for the transdermal delivery of fluidic drugs and other medicinal compounds that utilize microneedle arrays. For example, microneedles have the advantage of causing less pain to the patient as compared to larger conventional needles. In addition, conventional subcutaneous (often intramuscular) delivery of fluidic drugs via a conventional needle acts to deliver large amounts of a fluidic drug at one time, thereby often creating a spike in the bioavailability of the drug. For drugs with certain metabolic profiles this is not a significant problem. However, many drugs benefit from having a steady state concentration in the patient's blood stream; a well-known example of such a drug is insulin.

In some situations, transdermal drug delivery apparatuses including microneedle arrays are intended to administer liquid formulations at a substantially constant rate over an extended period of time, across a broad application area. It may also be desirable in some situations for such microneedle arrays to discharge liquid formulations at relatively low pressures so that the liquid formulations are administered by way of capillary action. However, there are conflicting factors associated with flow through a microneedle array, such that the flow may be associated with too few of the microneedles of the micro needle array.

SUMMARY

One aspect of this disclosure is the provision of a drug delivery device including a microneedle array assembly adapted in a manner that seeks to uniformly administer a liquid formulation into a patient's skin across a broad area and at a relatively low pressure. The device may administer the liquid formulation into the patient's skin at a substantially constant rate over an extended period of time and across a broad application area, wherein the administration of the liquid formulation into the patient's skin may occur at a relatively low pressure, such as by way of capillary action.

For example, the microneedle array assembly may comprise at least one uniformity control membrane securely engaged against an upstream side of a microneedle array, and optionally an additional membrane may be draped over the downstream side of the microneedle array. The uniformity control membrane may be a track etched membrane, or the like, and the uniformity control membrane and the microneedle array may be cooperatively configured so that the resistance to flow through the uniformity control membrane is substantially greater than the resistance to flow through the microneedle array. These differences in flow resistance seek to facilitate, for example, the uniform administration of the liquid formulation into the patient's skin across a broad area and at a relatively low pressure, such as by way of capillary action. The administration of the liquid formulation into the patient's skin across the broad area may comprise the liquid formulation being administered by way of at least a majority of the microneedles of the microneedle array. That is, the number of participating microneedles may be increased, to providing a larger area of administration of the liquid formulation at low pressure.

The foregoing presents a simplified summary of some aspects of this disclosure in order to provide a basic understanding. The foregoing summary is not extensive and is not intended to identify key or critical elements of the invention or to delineate the scope of the invention. The purpose of the foregoing summary is to present some concepts of this disclosure in a simplified form as a prelude to the more detailed description that is presented later. For example, other aspects will become apparent from the following.

BRIEF DESCRIPTION OF THE DRAWINGS

In the following, reference is made to the accompanying drawings, which are not necessarily drawn to scale and may be schematic. The drawings are exemplary only, and should not be construed as limiting the invention.

DETAILED DESCRIPTION

Exemplary embodiments are described below and illustrated in the accompanying drawings, in which like numerals refer to like parts throughout the several views. The embodiments described provide examples and should not be interpreted as limiting the scope of the invention. Other embodiments, and modifications and improvements of the described embodiments, will occur to those skilled in the art, and all such other embodiments, modification, and improvements are within the scope of the present invention.

In the following, a very brief and general initial discussion of a drug delivery device 10 of a first embodiment is followed by more detailed discussions, such as more detailed discussions of some of the separate subassemblies of the device 10. Discussions directed primarily to structural features of the device 10 are followed by discussions more specifically directed to methods of this disclosure.

Figure 1:
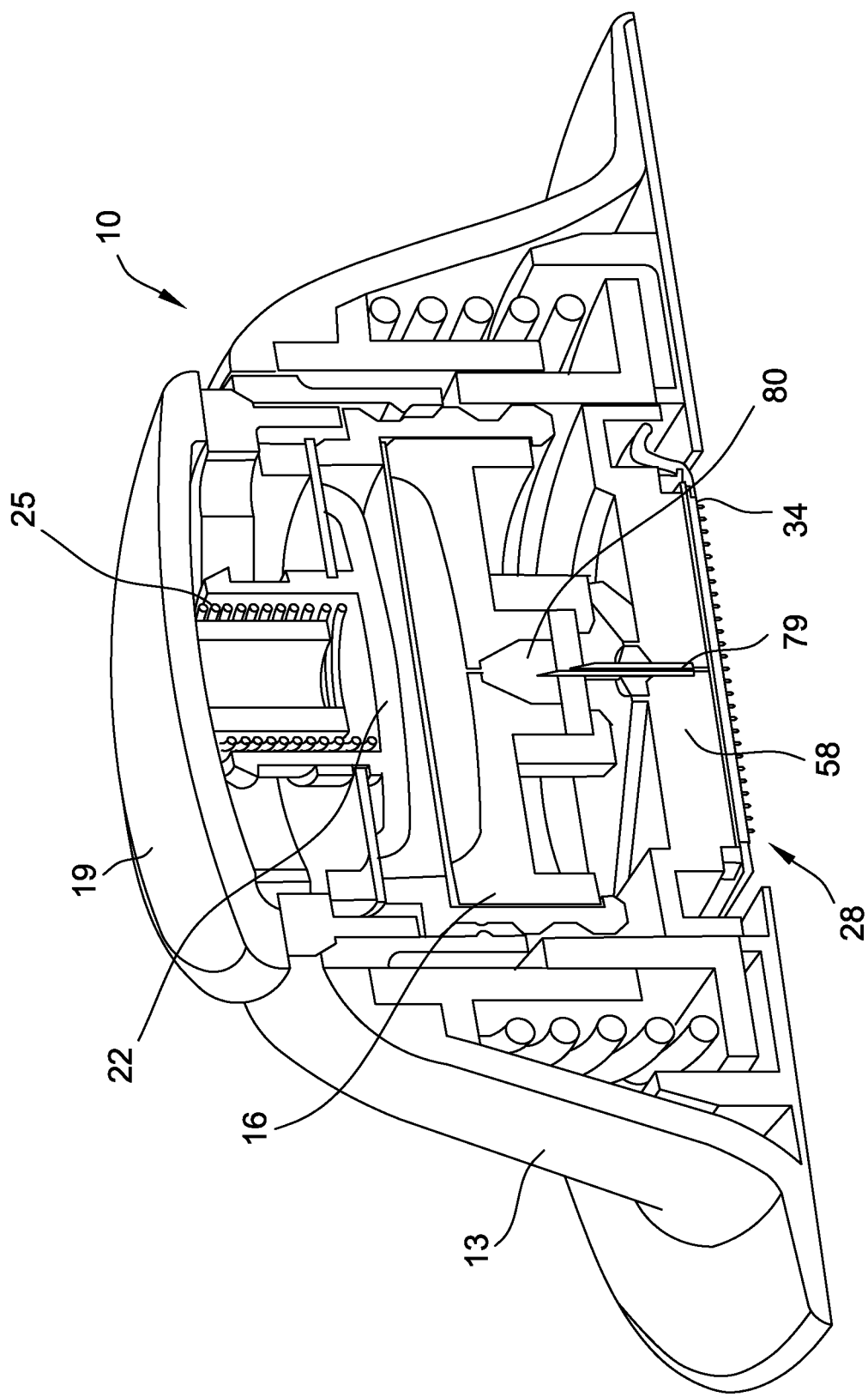
FIG. 1 is a cut-away view of a drug delivery device according to a first embodiment of this disclosure.

Referring to FIG. 1, the device 10 is shown in a partially activated configuration. The device 10 may be characterized as including multiple main subassemblies that each may be self-contained. The main subassemblies may include a receptacle 13, a cartridge 16 or other suitable container or reservoir for being movably mounted in the receptacle 13, and a mechanical controller 19 mounted to the cartridge 16.

The controller 19 can include a plunger 22 with, or alternatively without, an internal force provider 25. The controller 19 is for applying pressure to the reservoir or cartridge 16 and, thereby, assisting in discharging of a liquid drug formulation, or any other suitable liquid formulation, from the cartridge 16 to a microneedle array 28.

The receptacle 13 of the first embodiment includes the microneedle array 28. The microneedle array 28 includes a large number of microneedles 31 (FIG. 2) for penetrating the user's skin, such as for providing a fluid that may be in the form of a liquid drug formulation into the user's skin. The microneedle array 28 may be more generally referred to as a device for engaging the skin of a patient or other user, and dispensing the liquid formulation to the user's skin, such as by dispensing the liquid formulation into the epidermis portion of the user's skin. In contrast to how the device 10 is shown in FIG. 1, it is typical for at least a portion of the microneedles 31 of the microneedle array 28 to be protruding outwardly through a lower opening of the receptacle 13. An example of the device 10 is further described in U.S. Provisional Patent Application Nos. 61/996,149, 61/996,156, 61/996,157, and 61/996,158, each of which is incorporated herein by reference in its entirety.

Figure 3:
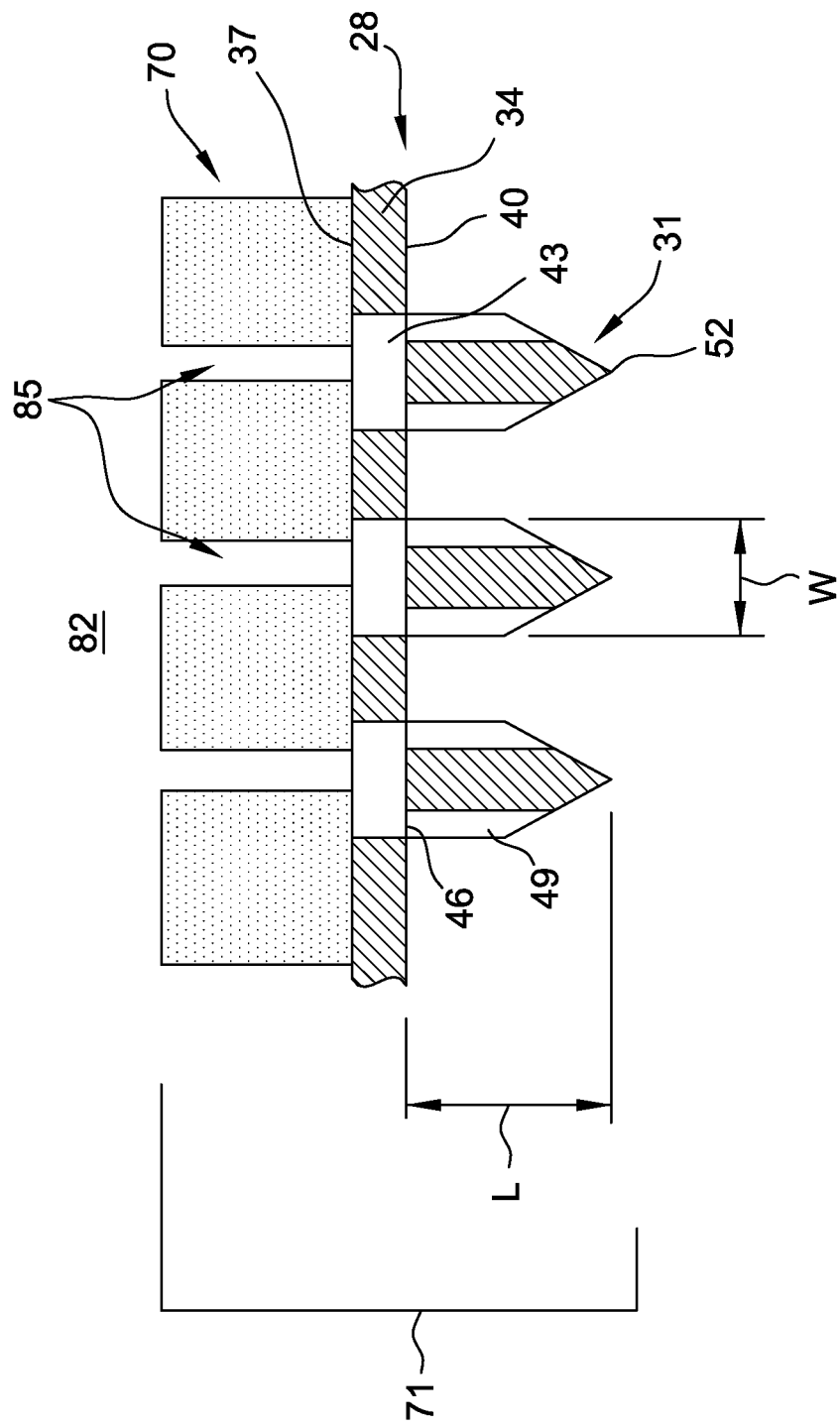
FIG. 3 is a more detailed, schematic cross-sectional view of a portion of a microneedle array assembly shown in FIG. 2.

As examples, the micro needle array 28 may be configured as disclosed in one or more of WO 2012/020332 to Ross, WO 20111070457 to Ross, WO 2011/135532 to Ross, US 2011/0270221 to Ross, US 2013/0165861 to Ross, and U.S. provisional patent application No. 61/996,148, each of which is incorporated herein by reference in its entirety. Generally, the microneedle array 28 of the device 10 may have any suitable configuration known in the art for delivering a liquid formulation onto, into, and/or through the user's skin, such as by being configured to include the plurality of microneedles 31 extending outwardly from a suitable substrate or support, wherein this substrate or support may be referred to as a base or base plate 34. As shown in FIG. 3, the base plate 34 has a top surface 37 (e.g., upstream side) and a bottom surface 40 (e.g. downstream side), and multiple microneedles 31 extend outwardly from the bottom surface. The base plate 34 and microneedles 31 may generally be constructed from a rigid, semi-rigid or flexible sheet of material, such as a metal material, a ceramic material, a polymer (e.g., plastic) material and/or any other suitable material. For example, the base plate 34 and microneedles 31 may be formed from silicon by way of reactive-ion etching, or in any other suitable manner.

The base plate 34 typically defines a plurality of passageways, which may be referred to as holes or apertures 43, extending between the top and bottom surfaces 37, 40 for permitting the liquid formulation to flow therebetween. For example, a single aperture 43 may be defined in the base plate 34 proximate each microneedle 31. However, in other embodiments, the base plate 34 may define any other suitable number of apertures 43 positioned at and/or spaced apart from the location of each microneedle 31. In the first embodiment, each aperture 43 leads to or includes a pair of downstream openings or exit openings 46 that are open to exterior channels 49 that are defined in and extend along each of the microneedles 31. Alternatively, each aperture 43 may extend through the base plate 34 as well as through the microneedle 31, as will be discussed in greater detail below.

Each microneedle 31 of the microneedle array 28 may include a base that extends downwardly from the bottom surface 40 and transitions to a piercing or needle-like shape (e.g., a conical or pyramidal shape or a cylindrical shape transitioning to a conical or pyramidal shape) having a tip 52 that is distant from the bottom surface 40. The tip 52 of each microneedle 31 is disposed furthest away from the base plate 34 and may define the smallest dimension (e.g., diameter or cross-sectional width) of each microneedle 31. Additionally, each microneedle 31 may generally define any suitable length L between its base and its tip that is sufficient to allow the microneedles 31 to penetrate the stratum corneum and pass into the epidermis of a user. It may be desirable to limit the length of the microneedles 31 such that they do not penetrate through the inner surface of the epidermis and into the dermis, which may advantageously help minimize pain for the patient receiving the liquid formulation.

Each microneedle 31 may have a length L of less than about 1000 micrometers (um), such as less than about 800 um, or less than about 750 um, or less than about 500 um (e.g., a length ranging from about 200 um to about 400 um), or any other sub-ranges therebetween. In one specific example, the microneedles 31 may have a length L of about 290 um. The length of the microneedles 31 may vary depending on the location at which the device 10 is being used on a user. For example, the length of the microneedles 31 for a device 10 to be used on a user's leg may differ substantially from the length of the microneedles for a device 10 to be used on a user's arm. Each microneedle 31 may generally define any suitable aspect ratio (i.e., the length L over a cross-sectional width dimension W of each microneedle 31). The aspect ratio may be greater than 2, such as greater than 3 or greater than 4. In instances in which the cross-sectional width dimension (e.g., diameter) varies over the length of each microneedle 31, the aspect ratio may be determined based on the average cross-sectional width dimension.

Each microneedle 31 may define the one or more exterior channels 49 in fluid communication with the apertures 43 defined in the base plate 34. In general, the exterior channels 49 may be defined at any suitable location on each microneedle 31. For example, the exterior channels 49 may be defined along an exterior surface of each microneedle 31 as seen in FIG. 3. As a more specific example, each exterior channel 49 may be an outwardly open flute defined by the exterior surface of, and extending along the length of, a microneedle 31. Alternatively and/or in addition, the channels 49 may be defined through the interior of the microneedles 31 such that each microneedle forms a hollow shaft, in which case the aperture 43 and the interior channel may have the same diameter and be coaxial, as generally discussed in greater detail below. Regardless, the exterior channels 49 in combination with the apertures 43 may generally be configured to form a downstream pathway that enables the liquid formulation to flow from the top surface 37 of the base plate 34, through the apertures 43 and into the channels 49, at which point the liquid formulation may be delivered onto, into, and/or through the user's skin. The exterior channels 49 may be configured to define any suitable cross-sectional shape. For example, each exterior channel 49 may define a semi-circular or circular shape. Alternatively, each exterior channel 49 may define a non-circular shape, such as a "v" shape or any other suitable cross-sectional shape.

The dimensions of the exterior channels 49 defined by the microneedles 31 may be specifically selected to induce a capillary flow of the liquid formulation. The capillary pressure within an exterior channel 49 is inversely proportional to the cross-sectional dimension of the exterior channel and directly proportional to the surface energy of the subject liquid, multiplied by the cosine of the contact angle of the liquid at the interface defined between the liquid and the exterior channel. Thus, to facilitate capillary flow of the liquid formulation through the microneedle array 28, the cross-sectional width dimension of the exterior channel(s) 49 (e.g., the diameter of the exterior channel) may be selectively controlled, with smaller dimensions generally resulting in higher capillary pressures. For example, the cross-sectional width dimension of the exterior channels 49 may be selected so that, with regard to the width of each exterior channel 49, the cross-sectional area of each exterior channel ranges from about 1,000 square microns ($um^2$) to about 125,000 $um^2$, such as from about 1,250 $um^2$ to about 60,000 $um^2$, or from about 6,000 $um^2$ to about 20,000 $um^2$, or any other sub-ranges therebetween.

The microneedle array 28 may generally include any suitable number of microneedles 31 extending from its base plate 34. For example, the actual number of microneedles 31 included within the microneedle array 28 may range from about 10 micro needles per square centimeter ($cm^2$) to about 1,500 microneedles per $cm^2$, such as from about 50 microneedles per $cm^2$ to about 1250 microneedles per $cm^2$, or from about 100 microneedles per $cm^2$ to about 500 microneedles per $cm^2$, or any other sub-ranges therebetween. The microneedles 31 may generally be arranged on the base plate 34 in a variety of different patterns, and such patterns may be designed for any particular use. For example, in some embodiments, the microneedles 31 may be spaced apart in a uniform manner, such as in a rectangular or square grid or in concentric circles. In such embodiments, the spacing of the microneedles 31 may generally depend on numerous factors, including, but not limited to, the length and width of the microneedles 31, as well as the amount and type of liquid formulation that is intended to be delivered through or along the microneedles 31.

Figure 2:
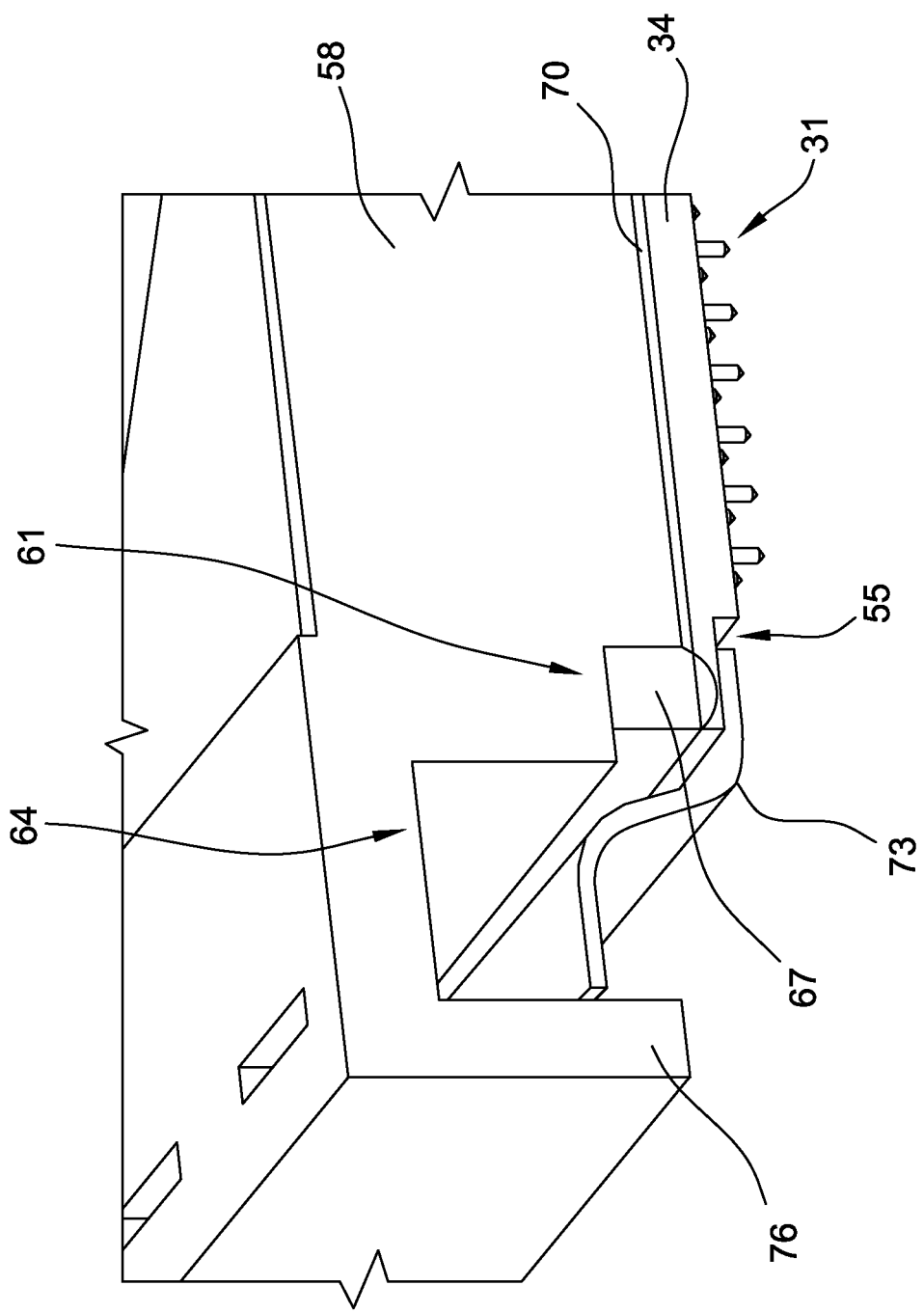
FIG. 2 is a detailed view of a portion of the device shown in FIG. 1.

As best understood with reference to FIG. 2, at least a portion of the micro needle array's base plate 34 may have a substantially rectangular periphery that is in the form of or includes a peripheral exterior channel 55 that (considering the base plate in isolation) is downwardly open and may have an overall substantially rectangular shape, or any other suitable shape. In the embodiment shown in FIG. 2, the microneedle array 28 is mounted to a backing structure 58 having inner and outer exterior channels 61, 64 that (considering the backing structure in isolation) are downwardly open and may have an overall rectangular shape, or any other suitable shape.

A substantially rectangular gasket 67 may be securely engaged in the backing structure's inner exterior channel 61 and engaged securely against the margin of at least one uniformity control membrane 70 that is engaged against and covers the top surface 37 of the microneedle array 28. These secure engagements associated with the gasket 67 may result at least partially from a frame 73 being fixedly mounted between the peripheral exterior channel 55 of the microneedle array 28 and the outer exterior channel 64 of the backing structure 58. The frame 73 may be mounted between the peripheral and outer exterior channels by way of one or more mechanical connections such as an interference fit and/or any other suitable fastening technique. In the first embodiment, the microneedle array 28 is substantially fixedly connected to the backing structure 58 of the support assembly of the receptacle 14 by way of the subject connections.

The frame 73 may be characterized as being a substantially rectangular bezel having substantially S-shaped cross-sections. The outer peripheral edge of the frame 73 may be press-fit into the outer exterior channel 64 so that the outer peripheral edge of the frame 73 is in compressing, opposing-face-to-face contact with a flange 76 that is part of or otherwise associated with (e.g., partially defines) the outer exterior channel 64, and the inner peripheral margin of the frame 73 is in compressing, opposing-face-to-face contact with the bottom surface 40 of the base plate 34. More specifically, the frame 73 engages against a surface of the peripheral exterior channel 55 of the base plate 34.

Referring back to FIG. 1, the receptacle 13 further includes at least one cannula 79 fixedly mounted to the backing structure 58 for moving therewith. For example, a lower portion of the cannula 79 may be fixedly mounted in a supply port extending through the backing structure 58 by way of one or more mechanical connections such as an interference fit, adhesive material and/or any other suitable fastening technique. The lower open end of the cannula 79 is in fluid communication with the upstream side of the uniformity control membrane 70 (FIG. 2), and the upper open end of the cannula 79, which is typically sharply pointed, extends axially upwardly from the backing structure 58 for piercing a predetermined portion of the cartridge 16 to access the reservoir 80 therein.

The combination of at least the microneedle array 28 and the uniformity control membrane 70 may be referred to herein as the microneedle array assembly 71. At least the backing structure 58 and the microneedle array assembly 71 are cooperatively configured so that a peripherally closed plenum chamber 82 (FIG. 3) is defined therebetween. The plenum chamber 82 is preferably hermetically sealed or closed, except for being open to a supply port such as provided by the cannula 79 extending through the backing structure 58, and being open to pores 85 (FIG. 3) of the uniformity control membrane 70.

During operation of the device 10 after it is configured as substantially shown in FIG. 1, the plunger 22 applies pressure to the cartridge 16 and the liquid formulation flows through the cannula 79 into the plenum chamber 82. The liquid formulation exits the plenum chamber 82 by flowing through pores 85 of the uniformity control membrane 70, and then the liquid formulation flows through the apertures 43 in the base plate 34 to the exterior channels 49 associated with the microneedles 31 and into the user's skin.

Reiterating from above and as shown in FIG. 3, the top surface 37 of the base plate 34 of the microneedle array 28 is covered with one or more uniformity control membranes 70 to at least partially form the microneedle array assembly 71. The uniformity control membrane 70 may be fabricated from permeable, semi-permeable or micro-porous materials configured for causing a pressure drop as the liquid formulation flows therethrough. In one example, at a predetermined flow rate with a predetermined drug formulation, an appropriate pressure drop across the uniformity control membrane 70 may be from 0.25 kPa to 50 kPa, from 10 kPa to 10 kPa, from 2.0 to 5.0 kPa, from about 0.25 kPa to about 50 kPa, from about 10 kPa to about 10 kPa, from about 2.0 to about 5.0 kPa, or any other subranges therebetween.

The uniformity control membrane 70 can be schematically modeled as having several discrete pores 85 for allowing the passage of liquid formulation from the plenum 82 (at the upstream side of the uniformity control membrane) to the apertures 43 (at the downstream side of the uniformity control membrane). In the first embodiment, the collective area of the pores 85 is less than the collective area of the apertures 43.

The uniformity control membrane 70 may be a track etched membrane. Track etched membranes provide an advantage because passage of the liquid formulation is generally limited to the direction through the thickness of the uniformity control membrane 70 from one side to the other, substantially preventing spread of the liquid formulation within the uniformity control membrane in a in a lateral direction perpendicular to the to the thickness of the uniformity control membrane. A suitable track etched membrane may be available from Sterlitech Corporation of Kent Wash., USA, and may be in the form of a 0.05 micron hydrophilic polycarbonate track etch membrane, or the like.

In the first embodiment, the uniformity control membrane 70 is associated with the top surface 37 of the backing structure 34 in a matter that limits or prevents lateral movement of the liquid formulation between the uniformity control membrane 70 and the base plate 34. In other words, liquid formulation associated with (e.g. proximate) one aperture 43 should be generally prevented from traveling over the top surface 37 into an adjacent aperture 43. When the uniformity control membrane 70 is a track etched membrane, it may have a smooth side and a rough side. Generally it is preferred to have the smooth side against the top surface 37 to avoid the undesired lateral flow of liquid formulation.

The uniformity control membrane 70 may be intimately held to the top surface 37 of base plate 34 by a pressing force applied by the frame 73 and gasket 67 around the periphery of the uniformity control membrane 70. During operation of the device 10, liquid pressure of the drug formulation within the plenum chamber 82 may be sufficient to hold the central area of the uniformity control membrane 70 against the top surface 37.

With reference back to FIG. 1, during operation of the device 10, the liquid formulation may be forced out of the cartridge 16 by the plunger 22 and the internal force provider 25 of the controller 19 to cause the liquid formulation to substantially uniformly fill the plenum chamber 82 (FIG. 3) and substantially uniformly wet the uniformity control membrane 70. In other words and referring to FIG. 3, the liquid formulation typically becomes available to each aperture 43 at the top surface 37 of the base plate 34. Referring to FIG. 1, the internal force provider 25 (e.g. at least one spring) functions in connection with the plunger 22 to provide substantially complete emptying of liquid formulation from the cartridge 16 through the cannula 79 and into the plenum chamber 82. The plunger 22 and internal force provider may provide a force in a range of 1.1 N to 1.3 N, about 1.1 N to about 1.3 N, 2 N to 2.2 N, about 2 N to about 2.2 N, 2.4 N to 2.6 N, about 2.4 N to about 2.6 N, 2.7 N to 2.9 N, about 2.7 N to about 2.9 Nor any other sub-ranges therebetween. The device 10 shown in FIG. 1 is provided as an example only. That is, the microneedle array assembly 71 may be used with or otherwise incorporated into any other suitable devices. For example, the plunger 22, force provider 25 and/or controller 19 may be replaced with other suitable features for forcing the liquid formulation into the plenum chamber 82, or the like.

The uniformity control membrane 70 may be selected so that the pressure drop resulting from the liquid formulation passing through the uniformity control membrane consumes substantially all of the pressure energy imparted into the liquid formulation by way of the plunger 22 and internal force provider 25. For example, the increase in pressure provided by the plunger 22 and internal force provider 25 may have an absolute value that is approximately equal to the absolute value of the decrease in pressure provided by the uniformity control membrane 70. In accordance in a method of operation of the first embodiment, the pressure remaining immediately downstream from the uniformity control membrane 70 may be only enough to cause or allow the liquid formulation to reach the channels 49 in a manner such that there is capillary flow of the liquid formulation in the exterior channels 49 of the microneedles 31.

Several variables should be considered together in order to produce the potentially desired capillary flow. For example, the larger the force applied by the plunger 22, the higher the pressure through the cannula 79 and the higher the pressure of the liquid formulation within the plenum 82. In order to maintain the target flow rate, the uniformity control membrane 70 should be capable of an increased pressure drop to compensate for the increased pressure within the plenum 82. As a result, the uniformity control membrane 70 typically has a resistance to flow that is selected in association with the plenum pressure and the subsystem that includes plunger 22 and force provider 25, if present.

Further regarding the microneedle array assembly 71 of the first embodiment and as best understood with reference to FIG. 3, the microneedle array assembly has numerous compound flow paths that extend through the microneedle array assembly, and each compound flow path may be characterized as including an upstream flow path and at least one downstream flow path. For each compound flow path extending through the microneedle array assembly 71, the upstream flow path may consist of one or more respective pores 85 of the uniformity control membrane 70, so that each of the upstream flow paths may be designated by the numeral 85. For each compound flow path extending through the microneedle array assembly 71, the at least one downstream flow path may comprise, consist essentially of, or consist of a respective aperture 43 and a respective one or more exit or downstream openings 46, so that each of the downstream flow paths may be designated by the numerals 43, 46, or just the numeral 43 for brevity. At least in theory, for each or a vast majority of the compound flow paths of the first embodiment, the downstream end of the upstream flow path 85 is in direct communication with the upstream end of the respective downstream flow path 43 for preventing lateral bypass flow, as generally discussed above.

Figure 4:
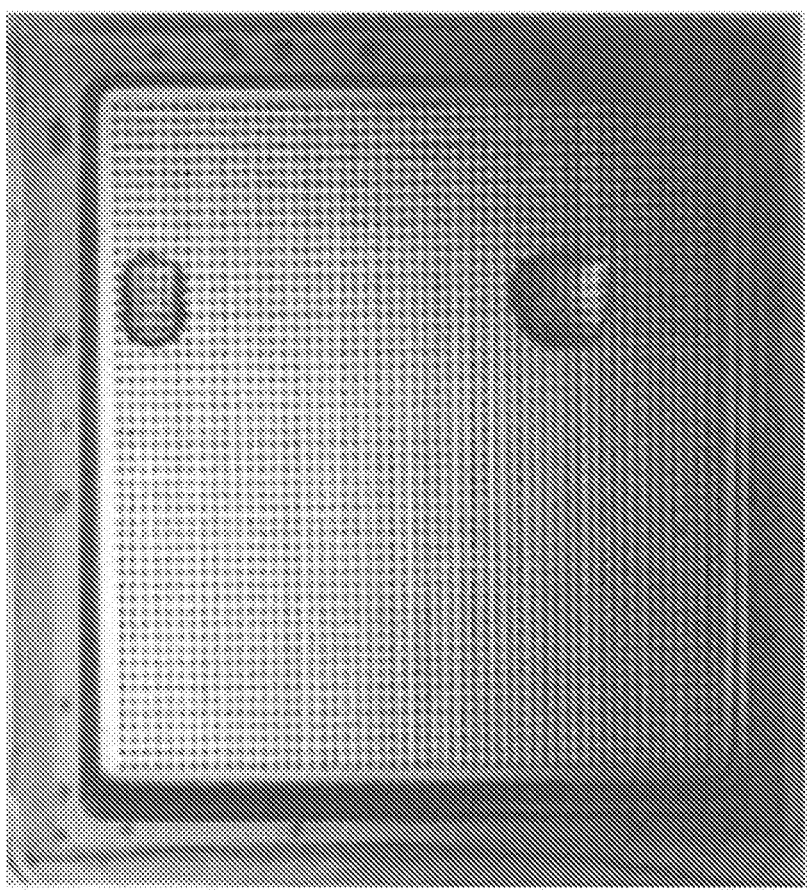
FIG. 4 shows the emission pattern of a microneedle array without a uniformity control membrane, as a comparative example.

As a first comparative example, FIG. 4 shows the downstream side of the microneedle array 28, wherein the uniformity control membrane 70 is not associated with the upstream side of the micro needle array, and the downstream side of the microneedle array is discharging water at a relatively low pressure, such as by way of capillary action, at a rate of about 200 µl/hr. As shown in FIG. 4 for the first comparative example, even though water is uniformly applied to the entire upstream side of the microneedle array 28, the water has flowed through the microneedle array at only a small number of discrete locations, so that the majority of the area of the microneedle array remains dry on the downstream side thereof. That is, FIG. 4 shows the water exiting out of a relatively small percentage of the downstream flow paths 43, such that the number of participating flow paths 43 is relatively small. This suggests that, for the first comparative example, there is a substantial lack of discharge uniformity through the microneedle array 28 and a greatly reduced efficiency of the broad application site of the microneedle array.

Manufacturing techniques typically limit the ability to form the downstream openings of the downstream flow paths 43 with exactly the same diameter or cross-sectional area, which in some situations may result a substantial lack of discharge uniformity, such as the lack of discharge uniformity shown in FIG. 4. More specifically regarding the fact that manufacturing techniques may limit the ability to form the downstream openings of the downstream flow paths 43 with exactly the same diameter or cross-sectional area, a bubble of the liquid formulation exiting from a relatively large downstream flow path 43 will have a larger bubble radius, and correspondingly, a smaller degree of surface tension, as compared to a bubble of the liquid formulation exiting from a relatively small downstream flow path 43. The energy required to add more liquid formulation to the larger bubble is less than the energy required to add liquid formulation to a smaller bubble pushing out from a smaller downstream flow path 43. In the first comparative example discussed above with reference to FIG. 4, the large bubble will grow slightly larger, and the pressure in that bubble decreases further. The result is that liquid formulation may flow through one or a few of the larger downstream flow paths 43, without flowing through the smaller downstream flow paths, even though the smaller downstream flow paths fully contain the liquid formulation.

In accordance with the first embodiment (e.g., in contrast to the comparative example of FIG. 4), the uniformity control membrane 70 may be adapted in a manner that seeks to increase the discharge uniformity through the microneedle array 28. For example, at least the uniformity control membrane 70 and the microneedle array 28 are cooperatively configured in a manner that seeks to allow the liquid formulation to be substantially uniformly administered across a relatively broad area and at a relatively low pressure, such as by way of capillary action, wherein the liquid formulation being substantially uniformly administered across the broad area comprises the liquid formulation steadily flowing through and exiting out of a relatively large percentage of the downstream flow paths 43, such that the number of participating downstream flow paths is relatively large. That is, the uniformity control membrane 70 may be configured to provide improved efficiency of the useful area of the microneedle array 28 relative to the first comparative example, by increasing the number of participating downstream flow paths 43 while maintaining a substantially similar target flow rate and relatively low administration pressure.

For each participating downstream flow paths 43, the liquid formulation may steadily flow through and exiting out of the flow path. That is, a participating downstream flow path 43 through the microneedle array 28 is a downstream flow path that has liquid formulation flowing therethrough and exiting therefrom. Increasing the number of participating downstream flow paths 43 means increasing the percentage of the downstream flow paths from which liquid formulation is flowing for a predetermined target flow rate and pressure. By increasing the number of participating downstream flow paths 43, administration of the liquid formulation can be considered as being more uniform across the area of the microneedle array 28. Because the body's response to a drug is area dependent, increasing the uniformity of discharge from the microneedle array 28 may improve the effectiveness of the drug formulation upon the body.

Using the uniformity control membrane 70 as herein described provides unexpected and critical improvements to the number of participating downstream flow paths 43 of the microneedle array 28 at a predetermined target flow rate and pressure. In this regard, the uniformity control membrane 70 may have a resistance to flow therethrough of at least about 30 times greater than, at least about 40 times greater than, at least about 50 times greater than, between about 30 and about 100 times greater than, between about 40 and about 100 times greater than, or between about 50 and about 100 times greater than the resistance to flow through the microneedle array 28. These resistances to flow and associated flow paths are discussed in greater detail below, sometimes with reference to the first embodiment, a second embodiment of this disclosure, the first comparative example, and a second comparative example.

The second embodiment of this disclosure may be like the first embodiment, except for variations noted and variations that will be apparent to those of ordinary skill in the art. Accordingly, reference numerals for features of the second embodiment that at least generally correspond to features of the first embodiment are incremented by one hundred.

Figure 5:
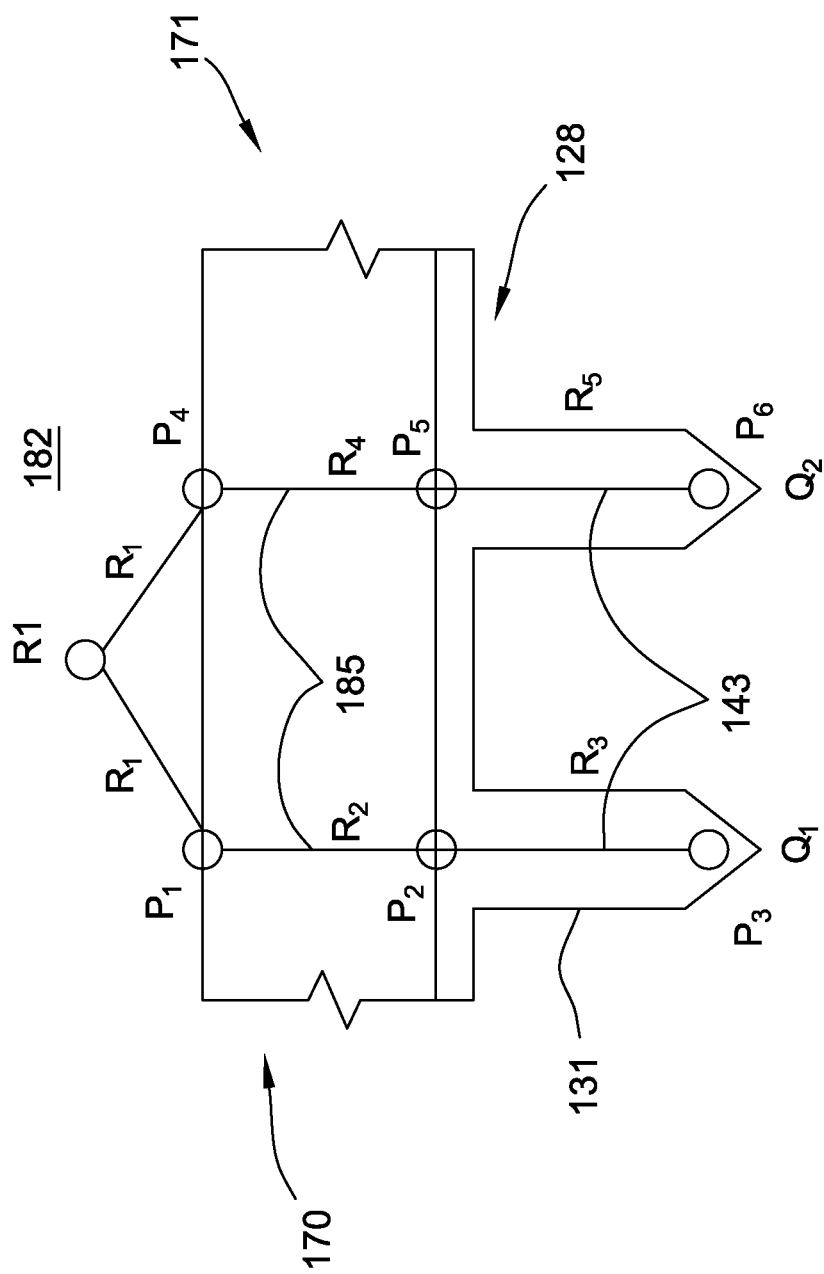
FIG. 5 is a diagrammatic representation of a portion of micro needle array assembly according to a second embodiment of this disclosure.

As diagrammatically shown in FIG. 5 for the second embodiment, each downstream flow path 143 of the microneedle array 128 may alternatively or optionally be in the form of an interior channel, wherein the interior channels extend through the interior of the microneedles 131 such that each microneedle forms a hollow shaft. That is, each downstream flow path 143 of the second embodiment may comprise an interior channel and, for example, the exterior channels 49 of the first embodiment may be omitted.

As an example, when the microneedle array assembly 171 is in use and the liquid formulation flows through the upstream flow paths 185 and reaches the upstream openings of the downstream flow paths 143, the liquid formulation will attempt to enter the upstream openings of the downstream flow paths 143. For example, when the contact angle that the liquid formulation makes with the downstream flow paths 143 is less than 90 degrees (e.g., when adhesive forces are stronger than the cohesive forces), the downstream flow paths 143 may fill up to the downstream openings of the downstream flow paths due to the due to capillary action. At this point, the downstream opening of each downstream flow path 143 can be generalized as having an independent boundary between the liquid formulation and the air. The boundary between a liquid (e.g., a liquid drug formulation) and a gas (e.g., air) has surface tension. When that boundary between the liquid and the gas is deformed, there is a change in surface tension due to a change in the curvature of the surface formed at the boundary. As the liquid formulation is pushed outwardly from the downstream openings of the downstream flow paths 143, the liquid formulation is pushed into the air and drops or bubbles of the liquid formulation can form exiting each downstream openings of the downstream flow paths. The curvature of these bubbles is small at first, and grows as liquid formulation flows through the downstream flow paths 143. However, as alluded to above, in some situations one of the exiting bubbles of the liquid formulation may be larger than the other, such as due to variations in sizes of the downstream openings of the downstream flow paths 143, or for one or more other reasons.

Some aspects of the factors associated with the flow of the liquid formulation and associated bubbles may be understood with reference to the theoretical system of FIG. 5 and the equations and calculations presented below. For the purposes of the following equations and calculations, the plenum chamber 182 and upstream and downstream flow paths 185, 143 are full of fluid, and there is a fluid/air interface at the downstream openings of the downstream flow paths. The flow through a first downstream flow path 143 is $Q_1$, and the flow through a second downstream flow path 143 is $Q_2$. $R_1$ represents any resistance to flow immediately upstream from the upstream openings of the upstream flow paths 185. $R_2$ and $R_4$ are the resistance to flow through the uniformity control membrane 170, or more specifically the resistance to flow through the upstream flow paths 185. $R_3$ is the resistance to flow through a first downstream flow path 143, and $R_5$ is the resistance to flow through a second downstream flow path 143. $P_{in}$ is the pressure at the source. $P_1$ and $P_4$ respectively are the pressures at the upstream openings of the upstream flow paths 185. $P_2$ and $P_5$ respectively are the pressures at the upstream openings of the downstream flow paths 143. $P_3$ and $P_6$ respectively are the pressures at the downstream openings of the downstream flow paths 143.

The pressures $P_3$ and $P_6$ respectively at downstream openings of the downstream flow paths 143 are typically neither constant nor zero. More specifically, these pressures $P_3$ and $P_6$ are respectively dependent on the shape of the fluid exiting the downstream openings of the of the downstream flow paths 143. In one example, the pressures $P_3$ and $P_6$ (e.g., the bubble pressures) at the downstream openings of the downstream flow paths 143 may each be about 1200 Pa, which represents the pressure required to push fluid out the downstream opening of each downstream flow path and into the air.

The pressures $P_3$ and $P_6$ respectively at the downstream openings of the downstream flow paths 143 may be calculated by the Young-Laplace equation which relates the surface tension, fluid curvature and pressure drop across the fluid/gas interface, as indicated below:

$$\Delta P = \gamma \left( \frac{1}{r_1} + \frac{1}{r_2} \right) \qquad \text{Equation 1}$$

In the above Young-Laplace equation, $r_1$ and $r_2$ are the principle radii of curvature of a bubble of the liquid formulation exiting the downstream opening of a downstream flow path 143. The radii of curvature change with the amount of fluid that has flowed. At low volumes the curvature is small and the pressure is large. As fluid flows the radius increases and the pressure is reduced.

It is the reduced pressure mentioned in the immediately prior sentence that may cause problems when attempting to administer liquid formulations at a relatively low pressure. For example, in the event that the downstream opening of the first downstream flow path 143 is slightly larger than the downstream opening of the second downstream flow path, the bubble pressure at the downstream opening of the first downstream flow path may be slightly less than the bubble pressure at the downstream opening of the second downstream flow path, so that the upstream liquid formulation may preferentially flow into the first downstream flow path. As a result, a large bubble of the liquid formulation at the downstream opening the first downstream flow path 143 may get larger, a small bubble of the liquid formulation at the downstream opening the second downstream flow path may get smaller, and the liquid formulation may flow through the first downstream flow path rather than the second downstream flow path. That is, the differences in bubble pressure may cause low uniformity of flow in microneedle array 128, as discussed above.

In accordance with one aspect of this disclosure, the uniformity control membranes 70, 170 may be configured in a manner that seeks to reduce the effects of differences in bubble pressure for optimizing the number of participating downstream flow paths 43, 143 at a predetermined target flow rate and pressure. For example, the uniformity control membranes 70, 170 may be advantageously configured in a manner that seeks to inhibit the pressure at the upstream opening of a downstream flow path 43, 143 from dropping substantially in response to flow through an adjacent downstream flow path, so that the flow through the adjacent downstream flow path does not negatively influence flow through the other downstream flow path. This relationship between a pair of adjacent downstream flow paths 43, 143 may be generally understood with reference the equations discussed below.

For the theoretical system of FIG. 5, the flow into the system is the sum of the flows through the first and second downstream flow paths 143, as indicated by the following equation:

$$Q_{in} = Q_1 + Q_2 \qquad \text{Equation 2}$$

Flow is proportional to the pressure drop and inversely proportional to the resistance. Accordingly, flow through first downstream flow path 143 may be determined from the following equation:

$$Q_1 = \frac{P_{in} - P_3}{R_1 + R_2 + R_3} \qquad \text{Equation 3}$$

Similarly, flow through the second downstream flow path 43 may be determined from the following equation:

$$Q_2 = \frac{P_{in} - P_6}{R_1 + R_4 + R_5} \qquad \text{Equation 4}$$

From the foregoing equations, sets of equations relating pressure drops, resistances, and flows may be produced and solved. For example, the following table represents values associated with a second comparative example that is based upon FIG. 5 but effectively does not include any uniformity control

| Second Comparative Example | |
|---|---|
| Input Data Set | Calculated Data Set |
| $Q_{in}$ = 100 ul/hr | $Q_1$ = 100.0 ul/hr |
| $P_{in}$ = 1,533.3 Pa | $Q_2$ = 0.0 ul/hr |
| $R_1$ = 2,000.00 Pa s/um³ | $P_1$ = 1,478 Pa |
| $R_2$ = 0.00 Pa s/um³ | $P_2$ = 1,478 Pa |
| $R_3$ = 10,000.00 Pa s/um³ | $P_4$ = 1,533 Pa |
| $R_4$ = 0.00 Pa s/um³ | $P_5$ = 1,533 Pa |
| $P_3$ = 1,200.00 Pa | |
| $P_6$ = 1,533.33 Pa | |

In accordance with the first and second embodiment, the uniformity control membranes 70, 170 may be configured in a manner that seeks to have the pressure at the upstream opening of one downstream flow path 43, 143 not change substantially in response to flow through an adjacent downstream flow path. In this regard, from the equations set forth above, an equation for determining $P_2$ may be derived, and it is set forth below:

$$P2 = \frac{P3(2R1 + R2 + R4 + R5) + R3(P6 + Qin(R1 + R4 + R5))}{2R1 + R2 + R3 + R4 + R5} \quad \text{Equation 5}$$

For determining how $P_2$ changes as $P_6$ changes, the above equation may be simplified by assuming that $R_1$ is equal to zero, $R_2$ and $R_4$ are equal to one another, and $R_3$ and $R_5$ are equal to one another, and the difference between $P_6$ and $P_3$ may be represented by β, to produce the following simplified equation:

$$P2 = P3 + \frac{R3(Qin(R2 + R3) + \beta)}{2(R2 + R3)} \quad \text{Equation 6}$$

From the above simplified equation, sets of equations may be produced and solved, for calculating the relationship between $P_2$ and the resistance of the uniformity control membrane 170 (i.e., $R_2$) and deviations in pressure between adjacent downstream openings of downstream flow paths 143 (i.e., β). For example, Equation 6 may be solved using $Q_{in}$ of 0.027 um³/s (i.e., 100 ul/hr), $P_3$ of 1200 Pa, and $R_3$ of 10,000 Pa s/um³, wherein the calculated relationships are shown in FIG. 6, with the upright axis (i.e., z-axis) representing $P_2$.

Figure 6:
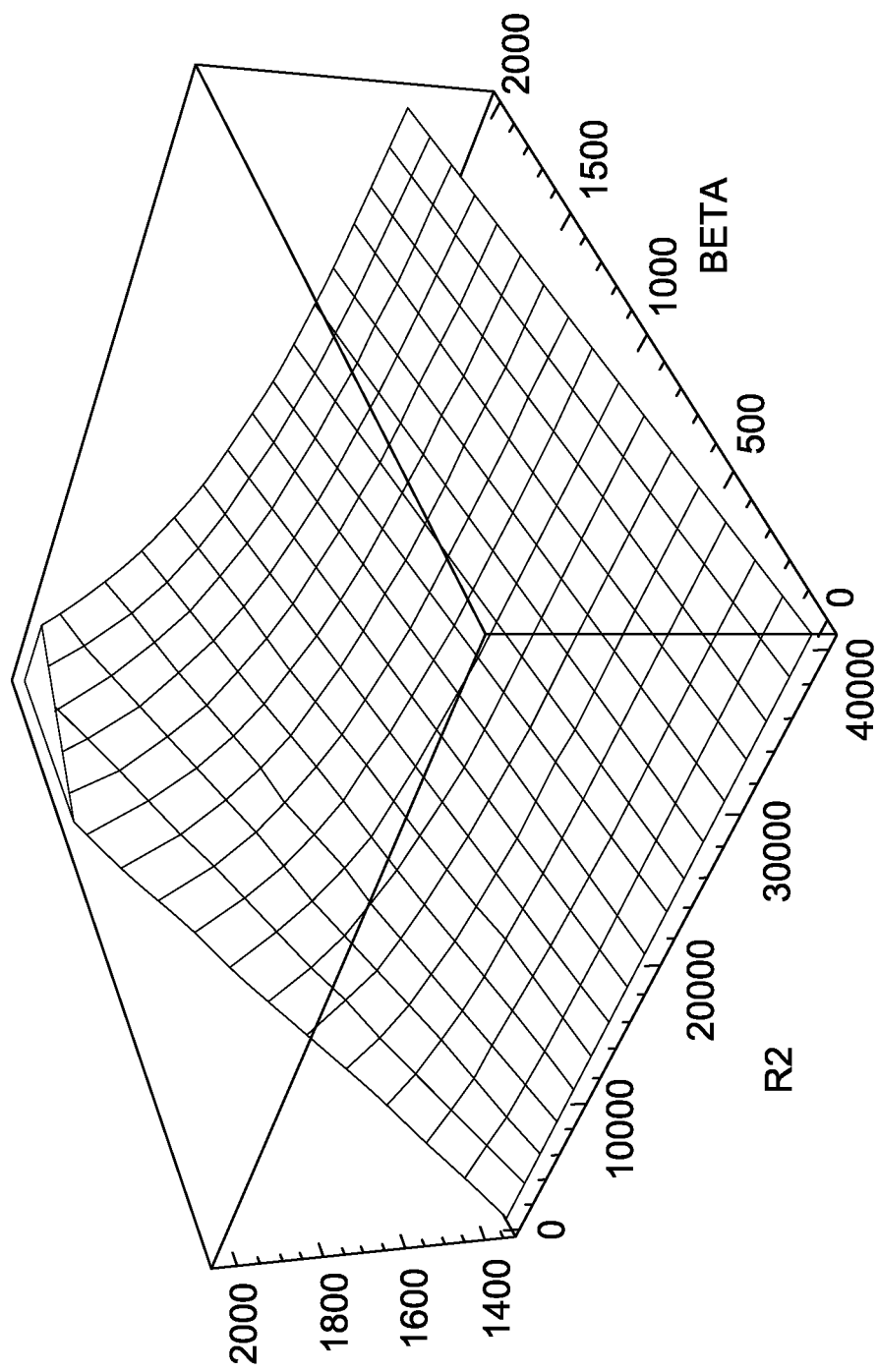
FIG. 6 is a graph that schematically illustrates how a suitably configured uniformity control membrane may seek to advantageously diminish the effects of variations in bubble pressures associated with microneedles of a microneedle array, in accordance with the second embodiment.

FIG. 6 schematically illustrates how suitably configured uniformity control membranes 70, 170 may seek to advantageously diminish the effects of variations in bubble pressures (e. g., β, or more specifically variations between $P_3$ and $P_6$) at downstream openings of downstream flow paths 143. For example and with reference to the system of FIG. 5 and Equation 6, the rate of change of $P_2$ as a function of differences between bubble pressures at adjacent downstream openings of downstream flow paths 143 (e.g., variations between $P_3$ and $P_6$, represented by β) may be represented by the following equation:

$$\frac{dP2}{d\beta} = \frac{R3}{2(R2 + R3)} \quad \text{Equation 7}$$

The foregoing equation provides insight into how a suitably configured uniformity control membrane 70, 170 may seek to advantageously diminish the effects of variations in bubble pressures (e.g., β, or more specifically variations between $P_3$ and $P_6$) at downstream openings of downstream flow paths 143. For example, if bubble pressures (e.g., β, or more specifically variations between $P_3$ and $P_6$) at downstream openings of downstream flow paths 143 vary by up to 1200 Pa and it is desirable for the pressure $P_2$ to deviate by less than 1%, Equation 7 may be represented as follows:

$$\frac{dP2}{d\beta} = \frac{0.1 * 1200}{1200} = \frac{R3}{2(R2 + R3)} \quad \text{Equation 8}$$

Equation 8 may be represented as shown below, for determining how much larger $R_2$ should be as compared to $R_3$, or more generally how much larger the resistance to flow through the uniformity control membranes 70, 170 should be as compared to the resistance to flow through the microneedle arrays 28, 128.

$$\frac{0.01 * 1200}{1200} = \frac{R3}{2(k * R3 + R3)} = \frac{1}{2(1 + k)} \quad \text{Equation 9}$$

Solving Equation 9 results ink being 49; therefore, in this example, $R_2$ should be at least about fifty times larger than $R_3$, or more generally the resistance to flow through the uniformity control membranes 70 and 170 should be at least about fifty times larger than the resistance to flow through the microneedle arrays 28 and 128, respectively. More generally, the uniformity control membranes 70 and 170 may have a resistance to flow therethrough of at least about 30 times greater than, at least about 40 times greater than, at least about 50 times greater than, between about 30 and about 100 times greater than, between about 40 and about 100 times greater than, or between about 50 and about 100 times greater than the resistance to flow through the microneedle arrays 28 and 128, respectively.

As alluded to above with reference to FIG. 5 and in accordance with one example, the pressures $P_3$ and $P_6$ (e.g., the bubble pressures of the fluid formulation) at the downstream openings of each of the downstream flow paths 43, 143 may be about 1200 Pa, which may represent the pressure required to push the fluid formulation out the downstream opening of the downstream flow path and into air. In examples of methods of operation, the pressure drop across the uniformity control membranes 70 and 170 may be at least about 30 times greater than, at least about 40 times greater than, at least about 50 times greater than, between about 30 and about 100 times greater than, between about 40 and about 100 times greater than, or between about 50 and about 100 times greater than the pressure required to push the fluid formulation out the downstream openings of the downstream flow paths 43, 143 and into air. The pressure required to push the fluid formulation out the downstream openings of the downstream flow paths 43, 143 and into air may be generally referred to as the bubble pressures of the microneedle arrays 28 and 128. Accordingly, the pressure drops across the uniformity control membranes 70 and 170 may be at least about 30 times greater than, at least about 40 times greater than, at least about 50 times greater than, between about 30 and about 100 times greater than, between about 40 and about 100 times greater than, or between about 50 and about 100 times greater than the bubble pressures of the microneedle arrays 28 and 128, respectively.

As alluded to above, for each compound flow path extending through the microneedle array assemblies 71, 171, the downstream openings of the upstream flow paths 85, 185 may be in direct communication with the upstream openings of the downstream flow paths 43, 143, for example as a result of the uniformity control membranes 70, 170 being securely engaged against the upstream sides of the microneedle arrays 28, 128. In accordance with one aspect of this disclosure and at least partially reiterating from above, the resistance to flow through the upstream flow paths 85, 185 may be substantially higher than the resistance to flow through the downstream flow paths 43, 143, wherein these differences in flow resistance seek to facilitate, for example, the uniform administration of the liquid formulation into the patient's skin across a broad area and at a relatively low pressure, such as by way of capillary action. The administration of the liquid formulation into the patient's skin across the broad area may comprise the liquid formulation being administered by way of at least a majority of the downstream flow paths 43, 143, such that the liquid formulation is administered by way of at least a majority of the microneedles of the microneedle arrays 28, 128.

That is, the uniformity control membranes 70, 170 may have the effect of significantly increasing the overall resistance to flow through each compound flow path (e.g., upstream flow paths 85, 185 together with downstream flow paths 43, 143) in a manner that minimizes differences in overall flow resistance among the numerous compound flow paths. As a result, the liquid formulation may actively utilize (i.e. flow through) an increased number of the compound flow paths when the liquid formulation is administered at a low pressure, such as a pressure that is low enough so that a substantial portion of the liquid formulation is administered by way of capillary action. That is, the number of participating compound flow paths may be increased to provide a larger area of administration of the liquid formulation at low pressure. The liquid formulation being administered by way of at least a majority of the downstream flow paths 43, 143 may comprise the liquid formulation being administered by way of at least about 50%, at least about 60%, at least about 70%, at least about 80% or at least about 90% of the downstream flow paths 43, 143.

In one aspect of this disclosure, when the liquid formulation is initially supplied to the upstream openings of the upstream flow paths 85, 185 and fills the compound flow paths, outwardly protruding bubbles of the liquid formulation may form at the downstream openings of the downstream flow paths 43, 143, and these bubbles contribute to the resistance to flow through the downstream flow paths 43, 143. In one example, the bubbles of the liquid formulation may be globules of the liquid formulation in the ambient atmosphere or environment, such as a thin layer of air covering a portion of a patient's skin where the liquid formulation is to be administered, or the like. Further regarding the outwardly protruding bubbles of the liquid formulation that initially form at the downstream openings of the downstream flow paths 43, 143, relatively small bubbles may form at some of the downstream openings, and relatively large bubbles may form at other of the downstream openings. The pressure of the liquid formulation in the relatively small bubbles is larger than the pressure of the liquid formulation in the relatively large bubbles, such that the resistance to flow due to the small bubbles is greater than the resistance to flow due to the large bubbles. At least in theory, the resistance to flow through the uniformity control membranes 70, 170 may be sufficiently large so that the pressure drop through the upstream flow path 85, 185 of a compound flow path with a relatively large and expanding bubble may exceed the pressure drop in the upstream portion of a compound flow path with a relatively small bubble. In this regard, the pressure drop in the upstream portion of the compound flow path with the relatively large and expanding bubble may exceed any pressure drop in the upstream portion of the compound flow path with the relatively small bubble in a manner that substantially equalizes the flow through the compound flow paths, so that a majority of the bubbles that form at the downstream openings of the downstream portions of the compound flow paths rupture and are replaced with a constantly outwardly flowing stream of the liquid formulation.

The above examples are in no way intended to limit the scope of the present invention. It will be understood by those skilled in the art that while the present disclosure has been discussed above with reference to exemplary embodiments, various additions, modifications and changes can be made thereto without departing from the spirit and scope of the invention, some aspects of which are set forth in the following claims.

We claim:

1. A microneedle array assembly, comprising:
   a microneedle array comprising
   a base having opposite upstream and downstream sides and defining a plurality of apertures extending between the upstream and downstream sides;
   a plurality of microneedles extending from the downstream side; and
   at least one membrane engaged against the upstream side of the base,
   wherein the microneedle array and the at least one membrane are cooperatively configured so that a plurality of flow paths extend through the microneedle array assembly, and the resistance to flow through the at least one membrane at the upstream side of the base is within a range of from about 30 times to about 100 times the resistance to flow through the microneedle array, wherein the about 30 times to about 100 times is a difference in the resistance to flow between the upstream side and the downstream side of the base, and wherein the difference is measured at the plurality of apertures of the base.

2. The microneedle array assembly of claim 1, wherein the resistance to flow through the at least one membrane is within a range of from about 40 times to about 100 times the resistance to flow through the microneedle array.

3. The microneedle array assembly of claim 1, wherein the resistance to flow through the at least one membrane is within a range of from about 50 times to about 100 times the resistance to flow through the microneedle array.

4. The microneedle array assembly of claim 1, wherein the at least one membrane being engaged against the upstream side of the base is comprised of a downstream side of the at least one membrane being engaged against the upstream side of the base in a manner that restricts any flow between the flow paths extend through the microneedle array assembly at an interface between the downstream side of the at least one membrane and the upstream side of the base.

5. A drug delivery device, comprising:
   a microneedle array assembly according to claim 1 and
   a reservoir operatively associated with the microneedle array for supplying liquid to the microneedle array by way of the at least one membrane.

6. The drug delivery device of claim 5, further comprising a force provider for causing at least some of the liquid to flow from the reservoir toward the microneedle array assembly.

7. The drug delivery device of claim 6, wherein:
   the force provider is for causing an increase in pressure of the liquid;
   the at least one membrane is for causing a decrease in pressure of the liquid; and
   an absolute value of the increase in pressure is approximately equal to an absolute value of the decrease in pressure.

8. The drug delivery device of claim 6, further comprising a plenum in fluid communication with an upstream side of the reservoir, wherein the force provider is for causing at least some of the liquid to flow from the reservoir to the plenum.

9. The drug delivery device of claim 8, further comprising a cannula in fluid communication with the plenum, wherein the drug delivery device is configured so that, in use, the liquid passes from the reservoir through the cannula into the plenum before passing through the at least one membrane and out the microneedle array.

10. A microneedle array assembly, comprising:
a microneedle array comprising
a base having opposite upstream and downstream sides and defining a plurality of apertures extending between the upstream and downstream sides;
a plurality of microneedles extending from the downstream side; and
at least one membrane engaged against the upstream side of the base,
wherein the microneedle array and the at least one membrane are cooperatively configured so that a plurality of flow paths extend through the microneedle array assembly, and the resistance to flow through the at least one membrane at the upstream side of the base is within a range of from about 30 times to about 100 times the resistance to flow through the microneedle array, wherein the about 30 times to about 100 times is a difference in the resistance to flow between the upstream side and the downstream side of the base, and wherein the difference is measured at the plurality of apertures of the base,
wherein the at least one membrane has a relatively smooth side and a relatively rough side, and the at least one membrane being engaged against the upstream side of the base is comprised of the smooth side of the at least one membrane being engaged against the upstream side of the base.

11. A microneedle array assembly, comprising:
a microneedle array comprising
a base having opposite upstream and downstream sides and defining a plurality of apertures extending between the upstream and downstream sides;
a plurality of microneedles extending from the downstream side; and
at least one membrane engaged against the upstream side of the base,
wherein the microneedle array and the at least one membrane are cooperatively configured so that a plurality of flow paths extend through the microneedle array assembly, and the resistance to flow through the at least one membrane at the upstream side of the base is within a range of from about 30 times to about 100 times the resistance to flow through the microneedle array, wherein the about 30 times to about 100 times is a difference in the resistance to flow between the upstream side and the downstream side of the base, and wherein the difference is measured at the plurality of apertures of the base,
wherein the at least one membrane is a track etched membrane.

* * * * *